(12) United States Patent
Wong et al.

(10) Patent No.: US 7,396,672 B2
(45) Date of Patent: Jul. 8, 2008

(54) METHOD FOR THE PRODUCTION OF DINOFLAGELLATE CULTURES

(75) Inventors: Tin Yum Joseph Wong, Flat 3A/T6, SSQ, Hong Kong University of Science & Technology, Clear Water Bay, Kowloon, Hong Kong (HK); Ka Kit Yeung, Hong Kong (HK); To Wai Francis Wong, Hong Kong (HK)

(73) Assignee: Tin Yum Joseph Wong, Kowloon, Hong Kong (CN)

( * ) Notice: Subject to any disclaimer, the term of this patent is extended or adjusted under 35 U.S.C. 154(b) by 330 days.

(21) Appl. No.: 10/675,004

(22) Filed: Sep. 30, 2003

(65) Prior Publication Data

US 2005/0070008 A1 Mar. 31, 2005

(51) Int. Cl.
*C12N 1/12* (2006.01)
*A01N 43/34* (2006.01)
(52) U.S. Cl. ............... 435/258.1; 435/244; 435/243
(58) Field of Classification Search ............... None
See application file for complete search history.

(56) References Cited

U.S. PATENT DOCUMENTS 5,407,957 A * 4/1995 Kyle et al. ............... 514/547
5,554,035 A * 9/1996 Gooch ............... 434/297
5,711,983 A 1/1998 Kyle et al.
6,432,468 B1 * 8/2002 Akimoto et al. ............... 426/614

OTHER PUBLICATIONS

Yeung et al., Applied and Environmental Microbiology, Oct. 2002, p. 5160-5163 vol. 68, No. 10.*
Godhe et al., Journal of Plankton Research vol. 23, No. 9 pp. 923-938.*
Berry et al., PNAS, 2002, vol. 99, No. 17, pp. 10970-10975.*
Martins et al., Brazilian J. of Biology, vol. 61, No. 4, 2001, pp. 1-9.*
Matsuoka et al., 2000, Technical Guide for Modern Dinoflagellate cyst Study.☐☐http://dinos.anesc.u-tokyo.ac.jp/technical_guide/main.pdf.*
ATCC Catalogue☐☐http://www.atcc.org/common/catalog/wordSearch/results.cfm☐☐.*
Godhe et al., Journal of Plankton Research vol. 23, No. 9 pp. 923-938, 2001.*
ATCC Catalogue☐☐http://www.atcc.org/common/catalog/wordSearch/results.cfm☐☐, date unknown.*

Brewbaker, J.L. 1989. Can there be such a thing as a perfect tree? Agroforestry Today 1: 4-7.
Chou, M.H., and C.G. Kuo 1986. Allelopathic Research of subtropical vegetation in Taiwan III. Allelopathic exclusion of understory by *Leucaena leucocephala* (Lam.) de Wit. J. Chem. Ecol. 12: 303-320.
Gilbert, D.M., A. Neilson, H. Miyazawa, M.L. DePamphilis, and W.C. Burhans. 1995. Mimosine arrests DNA synthesis at replication forks by inhibiting deoxyribonucleotide metabolism. J. Biol. Chem. 270: 9597-606.
John, E.H., and J.H. Flynn. 1999. Amino acid uptake by the toxic dinoflagellate *Alexandrium fundyense*. Mar. Biol. 133: 11-19.
Jones, R.J., and R.G. Megarrity. 1986. Successful transfer of DHP-degrading bacteria from Hawaiian goats to Australian ruminants to overcome the toxicity of *Leucaena*. Aust. Veterin. J. 63: 259-262.
Lin H.B., R. Falchetto, P.J. Mosca, J. Shabanowitz, D.F. Hunt, and J.L. Hamlin 1996. Mimosine targets serine hydroxymethyltransferase. J. Biol. Chem. 271: 2548-2556.
Mikhailov, I., G. Russev, and B. Anachkova. 2000: treatment of mammalian cells with mimosine generates DNA breaks. Mutation Res. 459: 299-306.
Rizzo, J. 1991. The enigma of the dinoflagellate chromosome. 1995. J. Protozool. 38: 246-252.
Raikov, I.B. 1995. The dinoflagellate nucleus and chromosomes: The mesokaryote concept reconsidered. Acta Protozoologica 34: 239-347.
Smayda, T.J. 1997. Harmful algal blooms: Their ecophysiology and general relevance to phytoplankton blooms in the sea. Limnol Oceanogr. 42: 1137-1153.
Soedarjo, M., and D. Borthakur. 1996. Simple procedures to remove mimosine from young leaves, pods and seeds of *Leucaena leucocephala* used as food. Int. J. Food Sci. and Technol. 31: 97-103.
Ter-Meulen, V.U., and E.A. El-Harith. 1985. Mimosine, a factor limiting the use of *Leucaena leucocephala* as an animal feed. Z. Landwirtschaft Tropen. Subtropen. 86: 109-127.
Tsai, W.C., and K.H. Ling. 1971. Toxic action of mimosine. I. Inhibition of mitosis and DNA synthesis of H.Ep-2 cell by mimosine and 3, 4-dihydroxypyridine. Toxicon 9: 241-247.

(Continued)

*Primary Examiner*—Irene Marx
(74) *Attorney, Agent, or Firm*—Alix, Yale & Ristas, LLP

(57) ABSTRACT

A method for selectively enhancing the growth of the population of a dinoflagellate comprises incubating a medium containing at least one dinoflagellate cell in the presence of mimosine or a toxic degradative product thereof is provided as well as isolates and cultures of dionoflagellates obtainable by said method. A method for isolating chemical compounds produced by dinoflagellates and chemical compounds obtainable by said method are also provided, as well as a method of identifying the causative agent of red tides.

15 Claims, 2 Drawing Sheets

OTHER PUBLICATIONS

Tuttle, R.C., and A.R. Loeblich. 1975. An optimal growth medium for the dinoflagellate *Crypthecodinium cohnii*. Phycologia 14: 1-8.

Wang, G., R. Miskimins, and W.K. Miskimins. 2000. Mimosine arrests cells in G1 by enhancing the levels of p27 (Kip1). Exp. Cell Res. 254: 64-71.

Wee, K.L., and S.S. Wang. 1987. Nutritive value of *Leucaena* leaf meal in pelleted feed for Nile tilapia. Aquaculture 62: 97-108.

Yoshida Y, Kodama K, Sakai Y, Tsujino K, Nakajima M, Yamamoto K, et al.: 1998. Relationship between the bloom of *Gymnodinium mikimotoi* and water quality or meteorological factors in Osaka Bay and Harima-nada. Bull. Japn. Soc. Scient. Fish. 64: 1006-1012.

Guillard R, and Ryther J: 1962. Studies of Marine Planktonic Diatoms. Canadian Journal of Microbiology. vol. 8: 229-239.

\* cited by examiner

METHOD FOR THE PRODUCTION OF DINOFLAGELLATE CULTURES

TECHNICAL FIELD

This invention relates to a method for obtaining high-purity isolates and cultures of dinoflagellates and to isolates and cultures obtainable by said method, to a method of isolating natural products produced by dinoflagellates and to natural products obtainable by said method, and to a method for identifying the causative dinoflagellate responsible for red tides.

BACKGROUND OF THE INVENTION

The dinoflagellates are important microscopic members of the planktonic community. There are believed to be over 2000 living species, including those of the genus *Gymnodinium, Karenia, Prorocentrum, Alexandrium, Symbiodinium, Crypthecodinium, Noctiluca, Gonyaulax, Protoperidinium, Gyrodinium, Amphidinium* and *Scrippsiella*. Primarily, though not exclusively, they are marine plankton. Non-photosynthetic dinoflagellates feed on diatoms or other protists. Many are photosynthetic and are important primary producers in coastal waters. Some are symbiotic, living in the cells of their hosts, such as corals and sea anemones.

Dinoflagellates are of importance for several reasons. First, they are known to produce a wide spectrum of bioactive natural products, including neurotoxins, some of which can act on humans (e.g. paralytic shellfish poisoning, the worst cases of which result in respiratory failure and death within 12 hours, ciguatera poisoning and diarrhetic shellfish poisoning). Some of these toxins are channel modulators (e.g. saxitoxins and maitotoxins) that are currently used in research on areas such as ion channel mechanisms. Furthermore, many have potentially useful pharmacological activity, e.g. the carbenolides and amphidinolides which show very promising anti-tumor properties.

Second, some dinoflagellates (e.g. species of the genus *Crypthecodinium*) produce large quantities of omega-3 fatty acids, particularly docosahexaenoic acid (DHA). These polyunsaturated fatty acids are known to be beneficial in reducing the incidence of coronary heart disease and are therefore included in a variety of health products. DHA is also used in infant formulas due to its high incidence in human milk and its implication in brain development.

Third, dinoflagellates are mainly responsible for the so-called red tides that occur in many seas worldwide. These red tides are caused by a massive multiplication (or "bloom") of dinoflagellates, usually in warm saltwater. The precise cause of these red tides is not known, although some experts believe that high temperatures combined with a lack of wind and rainfall are usually the catalysts for these blooms. These red tides can have major economic and health implications. The large quantities of toxins that are produced by the dinoflagellates in these red tides can not only kill a large range of marine species but they can also be accumulated in high concentrations in shellfish which are immune to the toxins and can result in severe digestive complaints, respiratory problems and even death in humans that eat these shellfish.

Because of their importance, it is desirable to produce live pure isolates and cultures of dinoflagellates, both to study them (to better understand red tides, for example), and to cultivate them to screen for bioactive natural products and to produce large quantities of high purity omega-3 fatty acids such as DHA. Unfortunately, until now it has been very difficult to generate such live pure isolates. This is due to the slow growth rate of dinoflagellates relative to other unwanted species of phytoplankton and to the inability of many dinoflagellates to grow in artificial media. The conventional method involves the isolation of individual cell(s) of the desired dinoflagellate from environmental samples. The pre-cultures are then incubated, either in seawater or other nutrient enrichments. However, as seawater and nutrient enrichments are not selective to dinoflagellates, other groups of faster-growing contaminating phytoplankton usually dominate or completely overtake the pre-cultures. Using such standard techniques, it typically takes a minimum of six months to scale up from a single-cell isolate to a 10 litre culture of the desired dinoflagellate. The success rate of making cultures from a single-cell isolate is typically of the order of 20%. Clearly, an improved method for the production of live pure isolates and cultures of dinoflagellates is highly desirable.

*Leucaena leucocephala* is a tropical and subtropical legume widely used in agroforestry systems throughout the world. It has been hailed as the perfect tree as it can serve many purposes, as foliage for livestock, as fuel wood or as green manure (1). Introduction of *Leucaena* outside its indigenous range has often led to acute and chronic toxicosis in animals (14). The agents of toxicity are the allelochemicals mimosine ($\alpha$-amino-3-hydroxy-4-oxo-1-pyridine propanoic acid), a non-protein amino acid, and its main degradative product 3,4-dihydroxypyridine (DHP) (2). The concentrations of mimosine in air-dried *Leucaena* leaves were found to be in the range of 2.5-5.75% (2) and can be easily removed by soaking in water for 24 h (2). Soil extracts from *Leucaena* plantation also have phytotoxicity to other plants (12). Mimosine and toxic degradative products thereof such as DHP are known to be toxic to all eukaryotic cells and most bacteria.

SUMMARY OF THE INVENTION

Tests were performed to investigate the use of mimosine to control phytoplankton growth. Surprisingly, it was found that not only does mimosine fail to inhibit the growth of dinoflagellates, but on the contrary it actually enhances their growth. Therefore, mimosine and toxic degradative products thereof can be used to promote the isolation and culture of dinoflagellates, enabling dinoflagellate isolates and cultures to be produced that are of a much higher purity than those obtainable using prior art methods. Furthermore, this method is considerably quicker than the prior art isolation and cultivation techniques.

The present invention thus relates to a method for the production of isolates and cultures of dinoflagellates using mimosine and toxic degradative products thereof to selectively promote the growth of said dinoflagellates relative to other unwanted microorganisms.

The present invention also relates to a method for the production of omega-3 fatty acids such as DHA comprising the cultivation of one or more dinoflagellate strains using mimosine to selectively promote the growth of said dinoflagellate strain or strains and then isolating from the dinoflagellate culture thus obtained said omega-3 fatty acid. The present invention also relates to omega-3 fatty acids obtainable by said method.

The present invention also relates to a method for the production of naturally occurring bioactive compounds such as saxitoxins and matotoxins produced by dinoflagellates comprising the cultivation of one or more dinoflagellate strains using mimosine to selectively promote the growth of said dinoflagellate strain or strains and then isolating from the dinoflagellate culture thus obtained said naturally occurring bioactive compounds. The present invention also relates to naturally occurring bioactive compounds obtainable by said method.

DETAILED DESCRIPTION OF THE INVENTION

Figure 1:
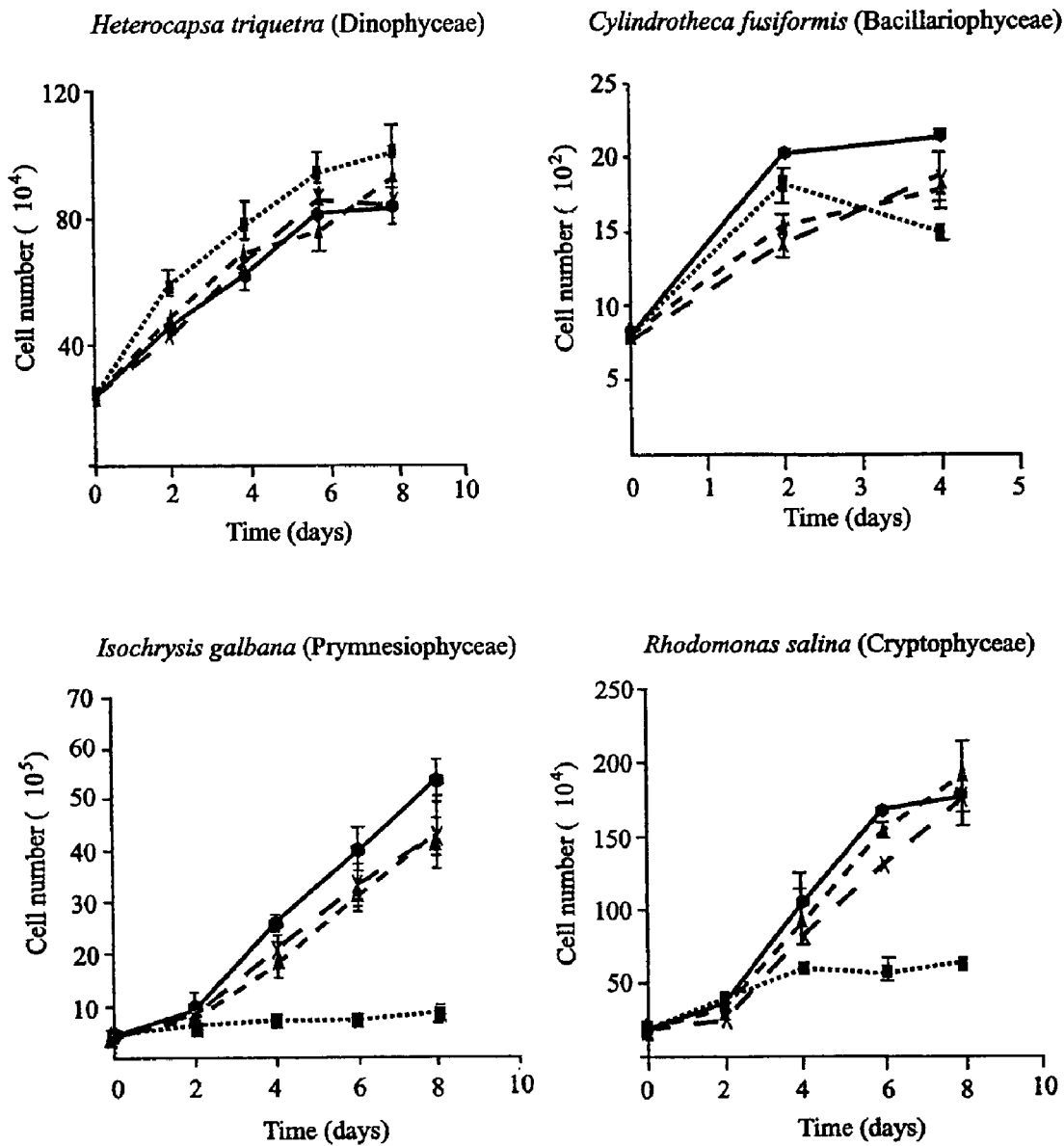
FIG. 1 shows the effects of mimosine on cell proliferation of monocultures of the major phytoplankton groups *Heterocapsa triquetra* (Dinophyceae), *Cylindrotheca fusiformis* (Bacillariophyceae), *Isochrysis galbana* (Prymnesiophyceae) and *Rhodomonas salina* (Crytophyceae)

Mimosine, the allelochemical from the tree-legume *Leucaena*, is toxic to most terrestrial animals and plants. We have found that while mimosine inhibits major phytoplankton groups, it enhances cell proliferation in dinoflagellates. On addition to coastal seawater samples, mimosine is able to confer growth advantage to the dinoflagellates. The use of mimosine promotes the isolation and culture of dinoflagellates.

Thus, in a first aspect of the invention there is provided a method for selectively enhancing the growth of the population of a dinoflagellate, said method comprising incubating a medium containing at least one dinoflagellate cell in the presence of mimosine or a toxic degradative product thereof.

The selective enhancement of the dinoflagellate growth is believed to be caused both by the toxicity of mimosine and toxic degradative products thereof to other major phytoplankton species that are contaminating the medium containing the dinoflagellate and by the positive stimulation of dinoflagellate cell proliferation.

In the present invention, mimosine ($\alpha$-amino-3-hydroxy-4-oxo-1-pyridine propanoic acid) or a toxic degradative product thereof is used to selectively enhance growth of the population of a dinoflagellate. The "toxic degradative product" is a product obtained by the degradation (e.g. by metabolism of mimosine or by chemical degradation) that, like mimosine itself, is toxic to other organisms in the medium containing the dinoflagellate but not to the dinoflagellate itself. Examples of such a toxic degradative product include 3,4-dihydroxypyridine. There is no particular limitation on the amount of mimosine or toxic degradative product used. Typically, however, selective enhancement of the growth of the dinoflagellate species can be obtained by the inclusion of mimosine or a toxic degradative product thereof in the medium containing said dinoflagellate at a concentration of from 0.001 mM to 50 mM. Preferably, the concentration of the mimosine or toxic degradative product thereof is from 0.01 mM to 20 mM. More preferably it is from 0.1 mM to 10 mM. Most preferably, it is from 1 to 5 mM.

The present invention can be used to selectively enhance the growth of any dinoflagellate. Examples of these dinoflagellates include those from a genus selected from the group consisting of *Gymnodinium, Karenia, Prorocentrum, Alexandrium, Symbiodinium, Crypthecodinium, Gonyaulax, Protoperidinium, Gyrodinium, Amphidinium* and *Scrippsiella*.

One embodiment of this aspect of the invention comprises selecting one or more dinoflagellate cells from a sample (typically with the aid of a microscope and a micropipette), placing said dinoflagellate cell or cells in a growth medium containing mimosine or a toxic degradative product thereof, incubating the mixture thus obtained until cell multiplication of the desired dinoflagellate is evident and, if necessary, transferring the enriched culture to fresh medium containing mimosine or a toxic degradative product thereof and repeating the sub-culturing of said enriched culture, until an isolate or culture of the required purity of the desired dinoflagellate is obtained. Usually, several rounds of sub-culturing in fresh medium are necessary to obtain high purity isolates and cultures.

The growth medium used in the present invention is any growth medium suitable for the cultivation of the desired dinoflagellate. Suitable growth media are well known to those in the art, e.g. the f/2 medium developed by Guilard and Ryther (20). Preferably, each sub-culturing round (i.e. the time taken from the transfer of the dinoflagellate to fresh medium to the point where cell multiplication of the desired dinoflagellate in the fresh medium is evident) is from 3 to 10 days, and more preferably it is from 4 to 7 days. The effects of the mimosine typically last for approximately 10 to 12 days, after which other the population of other phytoplankton groups starts to recover, hence the need to transfer the enriched culture to fresh medium once cell multiplication of the desired dinoflagellate is evident. Typically, the time needed to obtain a pure isolate or culture of the desired dinoflagellate using the method of the present invention is from 2 to 4 weeks, which is considerably faster than the 6 months that it takes using the prior art techniques.

Another embodiment of this aspect of the present invention comprises adding mimosine or a toxic degradation product thereof to a natural aquatic sample comprising one or more dinoflagellate cells, incubating the mixture thus obtained until cell multiplication of the desired dinoflagellate is evident, and isolating therefrom one or more cells of the desired dinoflagellate. In the present invention a "natural aquatic sample" is a sample obtained from a natural aquatic environment such as a sea, estuary, lake or river. Using this embodiment, it is thus possible to isolate known or novel dinoflagellates from natural aquatic samples, something that has been extremely difficult before because of the slow growth rate of dinoflagellates compared to other aquatic organisms. It is possible to obtain a high purity isolate or culture from the one or more cells of the dinoflagellate obtained by this method, by transferring said one or more cells to a growth medium containing mimosine or a toxic degradative product thereof, incubating the mixture thus obtained until cell multiplication of the desired dinoflagellate is evident and, if necessary, transferring the enriched culture to fresh medium containing mimosine or a toxic degradative product thereof and repeating the sub-culturing of said enriched culture, until an isolate or culture of the required purity of the desired dinoflagellate is obtained. Using this method, it has already been possible to isolate species of the genus *Gymnodinium, Karenia, Prorocentrum, Protoperidinium, Alexandrium* and *Symbiodinium*.

A further embodiment of the present comprises an isolate or culture of a dinoflagellate obtainable by a method of the first aspect of the present invention.

As already mentioned, dinoflagellates are important from an environmental and health perspective and also because they produce important bioactive products which have useful pharmacological activity and are utilized in research in areas such as ion channel mechanisms. Furthermore, some species of dinoflagellate produce polyunsaturated fatty acids such as omega-3 fatty acids (e.g. docosahexanoic acid) that are used in health products and infant formulas. The use of mimosine and toxic degradative products thereof to selectively enhance the growth of dinoflagellates gives access to high purity dinoflagellate cultures and isolates considerably more quickly and easily than has been achievable previously, and this can be utilized to isolate these bioactive compounds and unsaturated fatty acids in a more effective and efficient manner than has previously been possible.

Thus, in a further aspect of the invention there is provided a method for the isolation of a chemical compound produced by a dinoflagellate comprising selectively enhancing the growth of the population of said dinoflagellate by incubating a medium containing at least one cell of said dinoflagellate in the presence of mimosine or a toxic degradative product thereof, and isolating from the medium containing the dinoflagellate population thus obtained the desired chemical compound.

One embodiment of this second aspect of the invention is a method for the isolation of a chemical compound produced by a dinoflagellate, said method comprising selecting one or more dinoflagellate cells from a sample (typically with the aid of a microscope and a micropipette), placing said dinoflagellate cell or cells in a growth medium containing mimosine or a toxic degradative product thereof, incubating the mixture thus obtained until cell multiplication of the desired dinoflagellate is evident and, if necessary, transferring the enriched culture to fresh medium containing mimosine or a toxic degradative product thereof, repeating the sub-culturing of said enriched culture, until a culture of the desired dinoflagellate of suitable purity is obtained, and isolating from said culture of the desired dinoflagellate thus obtained the desired chemical compound.

Another embodiment of this aspect of this second aspect of the present invention comprises adding mimosine or a toxic degradation product thereof to a natural aquatic sample comprising one or more dinoflagellate cells, incubating the mixture thus obtained until cell multiplication of the desired dinoflagellate is evident and, if necessary, transferring the enriched culture thus obtained to fresh medium containing mimosine or a toxic degradative product thereof, repeating sub-culturing of said enriched culture, until a culture of the required purity of the desired dinoflagellate, and isolating from said culture of the desired dinoflagellate thus obtained the desired chemical compound.

In these two embodiments, the culture of "suitable purity" is one in which the percentage of the microorganisms present in the culture that are dinoflagellates is such that the desired chemical compound is produced in an amount that is sufficiently high to enable isolation thereof from the culture.

The chemical compound of interested can be isolated from the dinoflagellate culture by any technique conventionally used for this purpose. For example, one typical method for the isolation of the desired compound involves 1) filtration of the culture medium to remove any insolubles including the dinoflagellate biomass, 2) addition of water and an organic solvent immiscible with water such as benzene, diethyl ether, ethyl acetate or the like, to the aqueous mixture thus obtained, 3) extraction of the desired compound from the resulting mixture, 4) washing of the organic layer with water, 5) drying the organic layer over a desiccant such as anhydrous magnesium sulfate or the like, and 6) removal of the organic solvent. The desired compound thus obtained, if necessary, can be further purified by a conventional technique such as recrystallization, reprecipitation, silica gel column chromatography or high pressure liquid chromatography.

The method of this second aspect of the present invention can be used to isolate both known and novel chemical compounds produced by dinoflagellates. Bioactive compounds having useful properties can be isolated and purified relatively quickly and efficiently using the method of the present invention. Channel modulators (e.g. saxitoxins and maitotoxins) and protein phosphatase inhibitors (e.g. okadaic acid) that are currently used in research on ion channel mechanisms and tumor growth respectively can be isolated using this method. Many of the bioactive compounds that can be isolated from dinoflagellates using the method of the present invention have potentially useful pharmacological activity, e.g. the carbenolides such as carbenolide-I and amphidinolides such as amphidinolide A and amphidinolide B, which show very promising anti-tumor properties. Some dinoflagellates produce polyunsaturated fatty acids having useful properties, e.g species of the genus *Crypthecodinium* such as *Crypthecodinium cohnii* produce large quantities of omega-3 fatty acids, particularly docosahexaenoic acid (DHA), which are used in health products and infant formulas. The method of the present invention enables unsaturated fatty acids to be produced quickly and easily in large quantities.

A further embodiment of the present invention comprises a chemical compound produced by a dinoflagellate and obtainable by the method of the second aspect of the invention.

As explained earlier, dinoflagellates are mainly responsible for the so-called red tides that occur in many seas worldwide. These red tides can have major economic and health implications. Until now, it has been extremely difficult to manage red tides because it has been so difficult to isolate and identify the causative agent. The method of producing an isolate or culture of a dinoflagellate of the present invention is much quicker than prior art techniques, thus enabling much earlier identification of the causative agent of a red tide when it occurs and hence it may be easier to manage the problem as a result.

Thus, a third aspect of the present invention comprises a method for identifying the dinoflagellate responsible for a red tide comprising adding mimosine or a toxic degradation product thereof to a sample obtained from said red tide comprising one or more dinoflagellate cells, incubating the mixture thus obtained until cell multiplication of the dinoflagellate is evident and, if necessary, transferring the enriched culture thus obtained to fresh medium containing mimosine or a toxic degradative product thereof and repeating sub-culturing of said enriched culture, until a culture of sufficient purity to identify the dinoflagellate causing the red tide is obtained.

The present invention may be further understood by consideration of the following examples.

EXAMPLE 1

The Effects of Mimosine on Cell Proliferation of Monocultures of Major Phytoplankton Groups The effects of mimosine at low mM concentrations on pure cultures of four different groups of phytoplankton were tested. The phytoplankton tested were the Cryptophyceae *Rhodomonas salina* (CCMP1319), the Prymnesiophyceae *Isochrysis galbana* (CCMP1323), the Bacillariophyceae *Cylindricus fusiformis* (PCC100) and the dinoflagellate *Heterocapsa triquetra* (CCMP449). Cultures of phytoplankters were obtained from Bigelow Laboratory for Ocean Sciences (CCMP) or the Plymouth Culture Collection (PCC). The cultures were maintained in f/2 medium at 18° C., under photon flux of 50 mol·m$^{-2}$s$^{-1}$ from fluorescent tubes (Phillips daylight) under a 14:10 hours light/dark cycle. For cell proliferation assays, exponentially growing cells were diluted ten times with fresh medium before the addition of mimosine to give cultures having a final mimosine concentration of 0.01, 0.1 and 1 mM. All chemicals were from Sigma Corporation unless otherwise stated. All growth studies were performed in triplicate. Cell counting was performed by Coulter counter and all samples were counted at least three times.

In 0.01 and 0.1 mM mimosine, slightly lower numbers of cells, though not significantly so, were observed for *R. salina*, *I. galbana* and diatom *C. fusiformis* (see FIGS. 1*a-c*) when compared to the cell number in the control treatments in which no mimsine was added over the course of the experiment (8 days). At 1 mM mimosine, no cell number increase was observed for *I. galbana*. For *C. fusiformis* and *R. salina*, the mean cell numbers in 1 mM mimosine were significantly lower (25% and 75%) than those in the controls for these two phytoplnaktons. In the dinoflagellate *Heterocapsa triquetra* (CCMP449), however, not only did mimosine (1 mM) fail to have negative effects on cell proliferation, it surprisingly increased the cell number significantly when compared to the control treatment (see FIG. 1*d*).

EXAMPLE 2

The Effects of Mimosine on Mixed Phytoplankton in Natural Seawater Samples

Figure 2:
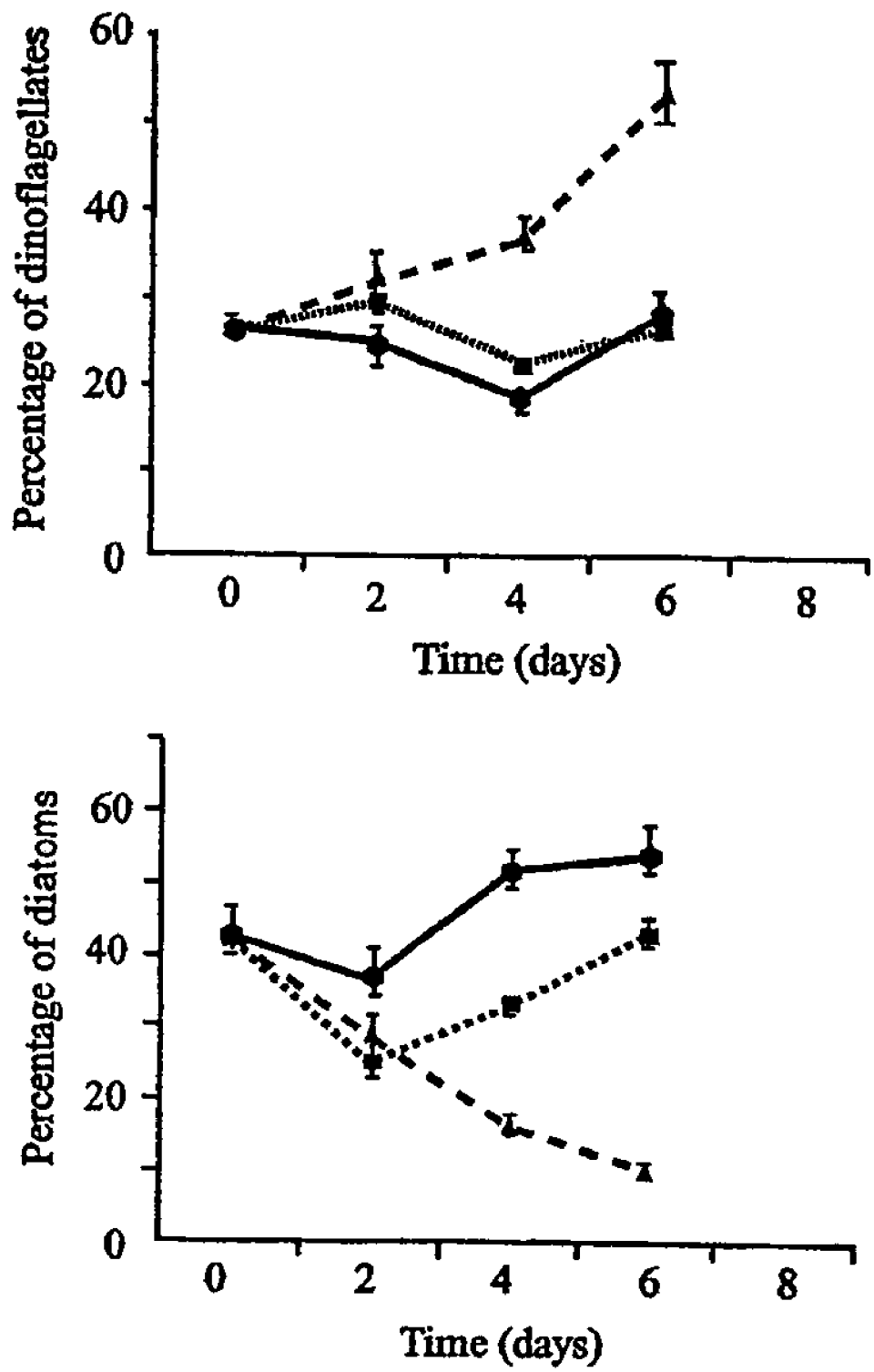
FIG. 2 shows the effects of mimosine on mixed phytoplankton in natural seawater samples.

The differential effects of mimosine on monocultures of phytoplankton groups suggests that it may have selective effects in mixed populations. Whether mimosine can confer an advantage in the phytoplankton community by adding mimosine directly to natural seawater samples was therefore tested. Natural seawater samples were collected from Port Shelter (eastern Hong Kong) and filtered through a 100 µm mesh to remove all zooplankton immediately before use. Mimosine was then added at 2 mM and samples were taken for estimation of the percentage of dinoflagellates and diatoms. The samples were then incubated under the same conditions as in Example 1. Within 6 days, dinoflagellates became the dominant group. The dinoflagellate population increased from 30% to 60% of the total population (FIG. 2). The diatoms, which were the dominant group in the control, decreased to 10% of the total population in 6 days (at the time of measurement) upon treatment with mimosine.

REFERENCES

1. Brewbaker, J. L. 1989. Can there be such a thing as a perfect tree? Agroforestry Today 1: 4-7.
2. Chou, M. H., and C. G. Kuo 1986. Allelopathic Research of subtropical vegetation in Taiwan III. Allelopathic exclusion of understory by *Leucaena leucocephala* (Lam.) de Wit. J. Chem. Ecol. 12: 303-320.
3. Gilbert, D. M., A. Neilson, H. Miyazawa, M. L. DePamphilis, and W. C. Burhans. 1995. Mimosine arrests DNA synthesis at replication forks by inhibiting deoxyribonucleotide metabolism. J. Biol. Chem. 270: 9597-606.
4. John, E. H., and J. H. Flynn. 1999. Amino acid uptake by the toxic dinoflagellate *Alexandrium fundyense*. Mar. Biol. 133: 11-19.
5. Jones, R. J., and R. G. Megarrity. 1986. Successful transfer of DHP-degrading bacteria from Hawaiian goats to Australian ruminants to overcome the toxicity of *Leucaena*. Aust. Veterin. J. 63: 259-262.
6. Lin H. B., R. Falchetto, P. J. Mosca, J. Shabanowitz, D. F. Hunt, and J. L. Hamlin 1996. Mimosine targets serine hydroxymethyltransferase. J. Biol. Chem. 271: 2548-2556.
7. Mikhailov, I., G. Russev, and B. Anachkova. 2000. Treatment of mammalian cells with mimosine generates DNA breaks. Mutation Res. 459: 299-306.
8. Oppenheim, E. W., I. M. Nasrallah, M. G. Mastri, and P. J. Stover. 2000. Mimosine is a cell-specific antagonist of folate metabolism. J. Biol. Chem. 275: 19268-19274.
9. Rizzo, J. 1991. The enigma of the dinoflagellate chromosome. 1995. J. Protozool. 38: 246-252.
10. Raikov, I. B. 1995. The dinoflagellate nucleus and chromosomes: The mesokaryote concept reconsidered. Acta Protozoologica 34: 239-347.
11. Smayda, T. J. 1997. Harmful algal blooms: Their ecophysiology and general relevance to phytoplankton blooms in the sea. Limnol. Oceanogr. 42: 1137-1153.
12. Soedarjo, M., and D. Borthakur. 1996. Simple procedures to remove mimosine from young leaves, pods and seeds of *Leucaena leucocephala* used as food. Int. J. Food Sci. and Technol. 31: 97-103.
13. Soedarjo, M., and D. Borthakur. 1998. Mimosine, a toxin produced by the tree-legume *Leucaena* provides a nodulation competition advantage to mimosine-degrading Rhizobium strains. Soil Biol. Biochem. 30: 1605-1613.
14. Ter-Meulen, V. U., and E. A. El-Harith. 1985. Mimosiine, a factor limiting the use of *Leucaena leucocephala* as an animal feed. Z. Landwirtschaft Tropen. Subtropen. 86: 109-127.
15. Tsai, W. C., and K. H. Ling. 1971. Toxic action of mimosine. I. Inhibition of mitosis and DNA synthesis of H. Ep-2 cell by mimosine and 3,4-dihydroxypyridine. Toxicon 9: 241-247.
16. Tuttle, R. C., and A. R. Loeblich. 1975. An optimal growth medium for the dinoflagellate *Crypthecodinium cohnii*. Phycologia 14: 1-8.
17. Wang, G., R. Miskimins, and W. K. Miskimins. 2000. Mimosine arrests cells in G1 by enhancing the levels of p27 (Kip1). Exp. Cell Res. 254: 64-71.
18. Wee, K. L., and S. S. Wang. 1987. Nutritive value of *Leucaena* leaf meal in pelleted feed for Nile tilapia. Aquaculture 62: 97-108.
19. Yoshida Y, Kodama K, Sakai Y, Tsujino K, Nakajima M, Yamamoto K, et al.: 1998. Relationship between the bloom of *Gymnodinium mikimotoi* and water quality or meteorological factors in Osaka Bay and Harima-nada. Bull. Japn. Soc. Scient. Fish. 64: 1006-1012.
20. Guillard, R. R. L. and Ryther, J. H. (1962). Studies on the marine planktonic diatoms. *I Cyclotella nana* Husted and *Detonela cofervacea* (Cleve). Can. J. Microb. 8: 229 239.

What we claim is:

1. A method for obtaining an isolated or purified culture of a dinoflagellate, said method comprising selecting one or more dinoflagellate cells from a sample, placing said dinoflagellate cell or cells in a growth medium containing mimosine or 3,4-dihydroxypyridine at a concentration of from 0.001 mM to 50 mM, culturing the mixture thus obtained in an incubator until cell multiplication of the dinoflagellate is evident thereby obtaining an enriched culture and, if necessary, transferring the enriched culture to fresh medium containing mimosine or 3,4-dihydroxypyridine at a concentration of from 0.001 mM to 50 mM and repeating the sub-culturing of said enriched culture, until an isolated or purified culture of the dinoflagellate is obtained.

2. The method of claim 1, wherein mimosine or 3,4-dihydroxypyridine, is present in said growth medium at a concentration of from 0.01 mM to 20 mM.

3. The method of claim 1, wherein mimosine or 3,4-dihydroxypyridine, is present in said growth medium at a concentration of from 0.1 mM to 10 mM.

4. The method of claim 1, wherein mimosine or 3,4-dihydroxypyridine, is present in said growth medium at a concentration of from 1 to 5 mM.

5. The method of claim 1, wherein from 1 to 3 rounds of transfer and sub-culturing of the desired dinoflagellate are performed.

6. The method of claim 1, wherein culturing the mixture in an incubator until cell multiplication of the dinoflagellate is evident takes from 3 to 10 days.

7. The method of claim 1, wherein culturing the mixture in an incubator until cell multiplication of the dinoflagellate is evident takes from 4 to 7 days.

8. A method for isolating one or more cells of a dinoflagellate from a natural aquatic sample, said method comprising adding mimosine or 3,4-dihydroxypyridine to a natural aquatic sample comprising one or more dinoflagellate cells at a concentration of from 0.001 mM to 50 mM, incubating the mixture thus obtained until cell multiplication of the desired dinoflagellate is evident, and isolating therefrom one or more cells of the desired dinoflagellate.

9. A method for obtaining an isolated or purified culture of a dinoflagellate from a natural aquatic sample, said method comprising adding mimosine or 3,4-dihydroxypyridine to a natural aquatic sample comprising one or more dinoflagellate cells at a concentration of from 0.001 mM to 50 mM, incubating the mixture thus obtained until cell multiplication of the desired dinoflagellate is evident, isolating therefrom one or more cells of the desired dinoflagellate, transferring said one or more cells to a growth medium containing mimosine or 3,4-dihydroxypyridine at a concentration of from 0.001 mM to 50 mM, incubating the mixture thus obtained until cell multiplication of the desired dinoflagellate is evident and, if necessary, transferring the enriched culture to fresh medium containing mimosine or 3,4-dihydroxypyridine at a concentration of from 0.001 mM to 50 mM and repeating the sub-culturing of said enriched culture, until an isolated or purified culture of the required purity of the desired dinoflagellate is obtained.

10. The method of claim 9, wherein mimosine or 3,4-dihydroxypyridine, is added in said natural aquatic sample and said growth medium at a concentration of from 0.01 mM to 20 mM.

11. The method of claim 9, wherein mimosine or 3,4-dihydroxypyridine, is added in said natural aquatic sample and said growth medium at a concentration of from 0.1 mM to 10 mM.

12. The method of claim 9, wherein mimosine or 3,4-dihydroxypyridine, is added in said natural aquatic sample and said growth medium at a concentration of from 1 to 5 mM.

13. The method of claim 9, wherein from 1 to 3 rounds of transfer and sub-culturing of the desired dinoflagellate are performed.

14. The method of claim 9, wherein each round of sub-culturing from said transfer to the point where cell multiplication of the desired dinoflagellate is evident is from 3 to 10 days.

15. The method of claim 9, wherein each round of sub-culturing from said transfer to the point where cell multiplication of the desired dinoflagellate is evident is from 4 to 7 days.

* * * * *